United States Patent
Hedner et al.

(10) Patent No.: US 10,617,694 B2
(45) Date of Patent: Apr. 14, 2020

(54) SULTIAME FOR THE TREATMENT OF SLEEP APNEA

(71) Applicants: Jan Hedner, Göteborg (SE); Ludger Grote, Göteborg (SE); Kaj Stenlöf, Torslanda (SE)

(72) Inventors: Jan Hedner, Göteborg (SE); Ludger Grote, Göteborg (SE); Kaj Stenlöf, Torslanda (SE)

( * ) Notice: Subject to any disclaimer, the term of this patent is extended or adjusted under 35 U.S.C. 154(b) by 0 days.

(21) Appl. No.: 16/300,651

(22) PCT Filed: May 9, 2017

(86) PCT No.: PCT/EP2017/061081
§ 371 (c)(1),
(2) Date: Nov. 12, 2018

(87) PCT Pub. No.: WO2017/194551
PCT Pub. Date: Nov. 16, 2017

(65) Prior Publication Data
US 2019/0201411 A1  Jul. 4, 2019

(30) Foreign Application Priority Data
May 11, 2016  (SE) ...................................... 1650636

(51) Int. Cl.
*A61K 31/54* (2006.01)
*A61K 9/00* (2006.01)
*A61P 11/00* (2006.01)

(52) U.S. Cl.
CPC ............ *A61K 31/54* (2013.01); *A61K 9/0053* (2013.01); *A61P 11/00* (2018.01)

(58) Field of Classification Search
CPC ........ A61K 31/54; A61K 9/0053; A61P 11/00
See application file for complete search history.

(56) References Cited

U.S. PATENT DOCUMENTS

| | | | |
|---|---|---|---|
| 2,916,489 A | 12/1959 | Helferich et al. | |
| 6,034,117 A | 3/2000 | Hedner et al. | |
| 8,071,557 B2 * | 12/2011 | Najarian | A61K 31/137 514/23 |
| 2004/0082519 A1 | 4/2004 | Hedner et al. | |
| 2007/0281005 A1 | 12/2007 | Grote et al. | |
| 2008/0261931 A1 | 10/2008 | Hedner et al. | |
| 2009/0304816 A1 | 12/2009 | Grote et al. | |
| 2011/0053914 A1 * | 3/2011 | Schiene | A61K 31/135 514/217 |
| 2011/0224196 A1 * | 9/2011 | Wilson | A61K 31/165 514/226.5 |
| 2016/0045527 A1 | 2/2016 | Bowden et al. | |

FOREIGN PATENT DOCUMENTS

| | | |
|---|---|---|
| JP | 2000-511873 A | 9/2000 |
| JP | 2003-523384 A | 8/2003 |
| JP | 2007-523079 A | 8/2007 |
| JP | 2009-508854 A | 3/2009 |
| JP | 2009-520023 A | 5/2009 |
| WO | WO-2011/085256 A2 | 7/2011 |

OTHER PUBLICATIONS

Temperini et. al., Bioorganic & Med. Chem. Letters, 2007, Elsevier, vol. 17, pp. 4866-4872 (Year: 2007).*
Eskandari et al., Zonisamide reduces obstructive sleep apnoea: a randomised placebo-controlled study, Eur. Respir. J., 44(1):140-9 (Jul. 2014).
Fine et al., Acetazolamide for electrical status epilepticus in slow-wave sleep, Epilepsia, 56(9):e134-8 (Sep. 2015).
Iber, The AASM manual for the scoring of sleep and associated events : rules, terminology and technical specifications, Westchester, Illinois: American Academy of Sleep Medicine (2007).
Lieberman et al. (eds.), Pharmaceutical Dosage Forms: Tablets, vols. 1 and 2, 2nd edition, New York: Marcel Dekker, Chapters 7, 8 and 9 (1989).
International Application No. PCT/EP2017/061081, International Search Report and Written Opinion, dated Jul. 4, 2017.
International Application No. PCT/EP2017/061081, International Preliminary Report on Patentability, dated Nov. 13, 2018.
Sakamoto et al., Effects of acetazolamide on the sleep apnea syndrome and its therapeutic mechanism, Psychiatry Clin. Neurosci., 49(1):59-64 (Mar. 1995).
Supuran, Carbonic anhydrases: novel therapeutic applications for inhibitors and activators, Nat. Rev. Drug Discov., 7(2):168-81 (Feb. 2008).
Tojima et al., Effects of acetazolamide in patients with the sleep apnoea syndrome, Thorax, 43(2):113-9 (Feb. 1988).
Winslow et al., A randomized, double-blind, placebo-controlled study of an oral, extended-release formulation of phentermine/topiramate for the treatment of obstructive sleep apnea in obese adults, Sleep, 35(11):1529-39 (Nov. 2012).
Australian Patent Application No. 2017261680, Examination Report No. 1, dated Sep. 20, 2018.
Japanese Patent Application No. 2018-554.36, Notice of Allowance, dated Feb. 4, 2019.
Korean Patent Application No. 10-2018-7028326, Notice of Patent Grant, dated Jan. 2, 2019.
Korean Patent Application No. 10-2018-7028326, Notice of Preliminary Rejection, dated Oct. 16, 2018.

* cited by examiner

*Primary Examiner* — Sarah Pihonak
(74) *Attorney, Agent, or Firm* — Marshall, Gerstein & Borun LLP

(57) ABSTRACT

There is provided for novel therapy of sleep apnea that involves administering the drug sultiame to the patient.

11 Claims, 1 Drawing Sheet

SULTIAME FOR THE TREATMENT OF SLEEP APNEA

FIELD OF THE INVENTION

This invention relates to the treatment of sleep apnea with the use of sultiame.

BACKGROUND

Sleep apnea (ICD-10: G47.3) is generally defined as an intermittent reduction or stop of airflow at the nose and mouth during sleep. Sleep apnea spans over a wide range of upper airway flow changes resulting in arousal of the patient (brief awakening from sleep), alteration of tissue blood gas and pH, as well as endocrine, paracrine, hemodynamic and vascular changes. In its simplest form sleep apnea may be characterized by subtle airflow restriction typically associated with sleep fragmentation that results in daytime sleepiness or various degrees of cognitive dysfunction.

Sleep apnea associated with daytime symptoms, specifically daytime hypersomnolence (sleepiness), is generally referred to as the Obstructive Sleep Apnea Syndrome (OSAS). Beside hypersomnolence, cognitive and mood changes provide a substantial burden on general health in patients with this condition. Hypersomnolence has been associated with complications including reduced working and driving performance, with an increased risk for accidents.

Moreover, cardiovascular complications, in particular hypertension, cardiac failure, cardiac arrhythmia, myocardial infarction and stroke have been strongly associated with sleep apnea.

Sleep apnea has furthermore been associated with increased insulin resistance, diabetes, obesity, changes in lipid metabolism, increased inflammation and platelet aggregation.

The prevalence of sleep apnea in the adult population depends on clinical laboratory cutoff values applied for the condition. Epidemiological studies suggest that sleep apnea defined as an apnea-hypopnea index (AHI) (number of apneas per hour of sleep) equal to or higher than 5 occurs in 24% of working adult men and in 9% of adult women.

The detailed pathophysiology of sleep apnea is unknown but is likely to include multiple mechanisms such as, but not limited to, dysfunctional chemical control of respiration, insufficient muscular control of the airway or structural anatomical obstruction of the airway during sleep, frequently caused by obesity or tonsillar hypertrophy.

In conclusion, sleep apnea is a significant clinical problem. Sleep apnea results in a considerably reduction of quality of life and a considerable risk of high blood pressure, myocardial infarction and stroke for a substantial part of the patients with this condition.

Despite intense research in the field there is no efficient pharmacological treatment for sleep apnea today.

The principal forms of treating or preventing sleep apnea includes surgery of the upper airway and use of medical devices (various forms of positive airway pressure (PAP) devices), intra-oral mandibular advancement devices, positional therapy and nerve stimulation devices.

Surgery is not uniformly effective. In particular, surgery is frequently associated with relapse of symptoms.

PAP treatment involves wearing a face mask that covers the airways during sleeping. Patients frequently find this therapy uncomfortable. Although often effective, this method has poor long-term compliance.

An intra-oral mandibular advancement device is a device that is worn in the mouth and which moves the lower jaw forward during sleep. These devises are frequently uncomfortable and low long-term compliance is moderate. Also, they are not always effective.

Positional therapy (trying to make patients to sleep on the side rather than on the back) may be partly effective in some patients. Long term compliance is low.

Hypoglossal and phrenic nerve stimulation are under development and is not always effective. Long term compliance is not fully characterized.

Various forms of pharmacological treatment, e.g., tricyclic antidepressants, theophylline, progesterone, zonisamide (Eskandari D et al, (2014) *Eur Respir J:* 44:140-149) and topiramate (together with another compound) (Winslow D et al, (2012) *Sleep* 35:11 1529-1539) have been tried. Zonisamide and topiramate both have carbonic anhydrase inhibitory activity as part of their activity profiles. However, these compounds have not gained any wide clinical use as efficacy has been limited and since side effects have been prominent. Both zonisamide and topiramate have cognitive side effects which due to their seriousness limit the use of these compounds in patients with sleep apnea. In addition, the use of topiramate has been associated with an increased risk of suicide. Zonisamide and topiramate are mainly used for the treatment of epilepsy, where these side effects have been considered acceptable from a risk-benefit perspective.

US20160045527 and WO 2011085256 each propose the use of carbonic anhydrase inhibitors such as topiramate or zonisamide in combination by co-administration with other compounds such as aldosterone antagonists or a non-benzodiazepine sedative agent for the treatment of sleep apnea. However, those patent applications are speculative as no experimental evidence is provided for efficacy or side effects.

Carbonic anhydrase catalyses the interconversion of $CO_2$ and water to bicarbonate and protons. There are at least sixteen carbonic anhydrase isoenzymes, and they all have different activity profiles. Several inhibitors of carbonic anhydrases are known. It has been acknowledged that that the inhibition profiles for the various carbonic anhydrase isoenzymes may explain the difference in efficacy in various clinical applications for the carbonic anhydrase inhibitors. (Supuran C., (2008) *Nature Reviews Drug Discovery*, February 2008, 168-181). Supuran further states that the various carbonic anhydrase inhibitors have been extensively studied and exploited for several diseases.

Acetazolamide, which is a prototype inhibitor of carbonic anhydrase, has been reported to be useful for the treatment of sleep apnea (Tojima H. et al, (1988) *Thorax;* 43:113-119). Acetazolamide is one of the most commonly used carbonic anhydrase inhibitors, and is the carbonic anhydrase inhibitor reported to most effectively reduce sleep apnea. Drawbacks of acetazolamide treatment include frequent occurrence of paraesthesia (a sensation of tingling, tickling, pricking, or burning) and these side effects limit a wide use of acetazolamide in the clinical setting. The use of acetazolamide for the treatment of sleep apnea has therefore not gained a wide acceptance.

In general, the current treatments for sleep apnea are associated with a number of drawbacks, and there is a need for novel treatments of sleep apnea. In particular there is a need for an improved pharmacological treatment of sleep apnea that brings improved efficacy and tolerable side effects, in particular lower frequency of paraesthesia.

It has now surprisingly been found that sultiame shows higher efficacy than acetazolamide in the treatment of sleep apnea. Sultiame has a high efficacy in sleep apnea and has a surprisingly favourable side effect profile. Sultiame (Sulthiam; Sultiam; Ospolot; Contravul; Sulphenyltame) (4-(1,1-dioxothiazinan-2-yl benzenesulfonamide) is a carbonic anhydrase inhibitor drug known since the 1950s. Today the use of sultiame is limited. Sultiame is mainly used for certain rare forms of childhood epilepsy (benign Rolando epilepsy, BECTS), in German-speaking countries.

SUMMARY OF INVENTION

In a first aspect of the invention it is provided sultiame for use in the treatment of sleep apnea. The sleep apnea can be obstructive sleep apnea, central sleep apnea or mixed sleep apnea. In a preferred embodiment the patient has an Apnea Hypopnea Index of 15 n/h or more (moderate or severe sleep apnea). In one embodiment the patient has an Apnea Hypopnea Index of from 15 n/h to 29 n/h (moderate sleep apnea), more preferably from 15 n/h to 20 n/h. In certain embodiments, the patient may preferably be a male patient. In certain embodiments the patient may preferably be overweight. For example the patient may have a body mass index (BMI) of at least 25.

Sultiame can be administered in various ways. Peroral administration may be preferred, since it is convenient for the patient. The daily dose may vary from 80 mg to 1000 mg. In one embodiment the daily dose may be from 80 mg to 250 mg. Preferably the daily dose is administered once per day.

In certain embodiments a high dose of sultiame may be preferred in order to treat sleep apnea, especially for treatment of patients having a high BMI. Thus in one embodiment the daily dose may be from 150 mg to 1000 mg, more preferably from 175 mg to 1000 mg, more preferably from 200 mg to 1000 mg, even more preferably from 250 mg to 1000 mg, even more preferably 300 mg to 1000 mg, and most preferably from 500 mg to 1000 mg.

Alternatively, in order to avoid side effects, the highest daily dose may be 800 mg, more preferably 600 mg, and most preferably 400 mg.

In one embodiment sultiame is used as a single agent, i.e. as the single active compound in a pharmaceutical composition. This has the advantage of minimizing side effects and also to minimize the risk of interaction with other drugs.

The treatment with sultiame may be used to treat sleep apnea, in particular improve residual sleep apnea or insufficiently treated sleep apnea in patients with ongoing nasal PAP therapy or treatment with an intraoral device.

The drug may be administered from 1 to 3 hours prior to the expected onset of sleep. This is a convenient way of administering the drug.

In a second aspect of the invention there is provided a method for treatment of sleep apnea involving administrating to a patient in need thereof a therapeutically effective amount of sultiame.

In a third aspect of the invention there is provided use of sultiame for the manufacture of a medicament for the treatment of sleep apnea.

In a fourth aspect of the invention there is provided a method for diagnosis of sleep apnea.

The invention provides for a convenient, user friendly and efficient treatment of sleep apnea.

DETAILED DESCRIPTION

Figure 1:
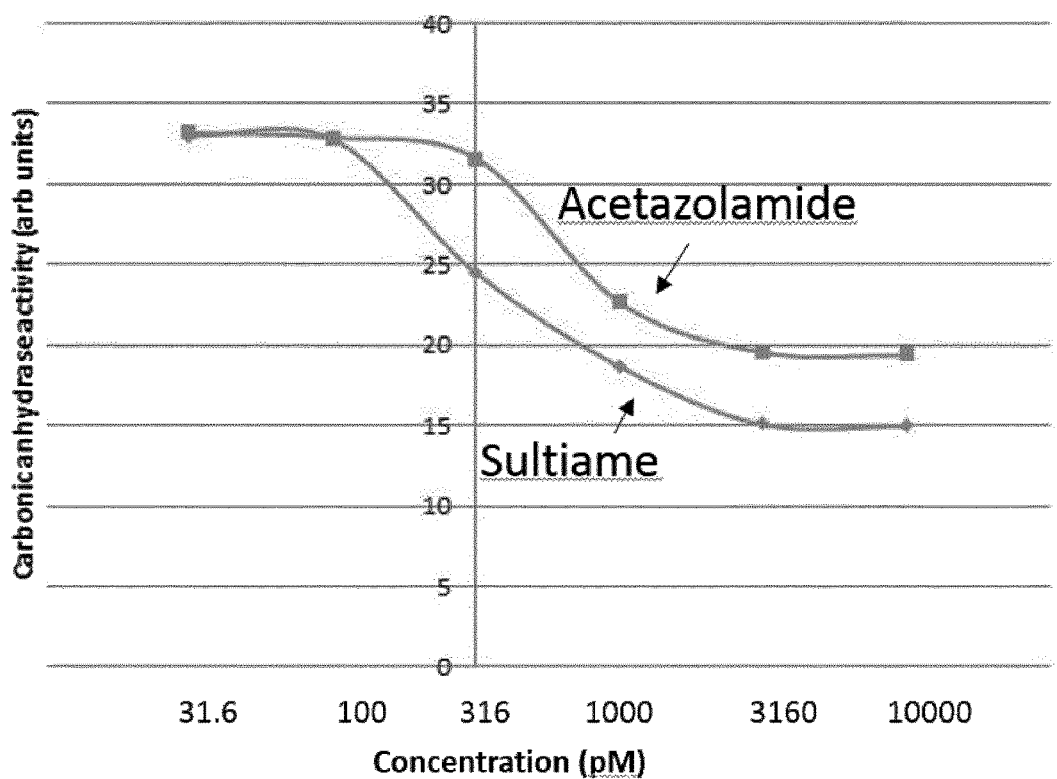
FIG. 1 shows carbonic anhydrase activity inhibition in plasma from a sleep apnea patient.

Continuous periods of apnea are referred to as apneic events. Their duration may vary but by convention, apneic events of at least 10 seconds in duration are considered significant. However, apneic events may extend up to 2-3 minutes and may cause complete (apnea) or partial (hypopnea) stop of airflow. In this application the term "apnea" shall also include hypopnea, and the term apneic event shall also include hypopneic event.

Sleep apneas are conventionally classified into three different types; central, obstructive and mixed. Central sleep apnea (CSA) is characterized by complete cessation of the activity of all respiratory muscles while in obstructive sleep apnea (OSA) airflow is interrupted despite continuing respiratory neural drive. OSA occurs as a result of occlusion of the upper airway, usually at the oropharynx, and is the most prevalent form of sleep apnea. Mixed apnea usually manifests itself as initial central sleep apnea followed by an episode of obstructive sleep apnea.

Methods for diagnosing sleep apnea are well known. Methods for diagnosis include counting the number of apnea events per hour (AHI) in a sleep study involving the patient. Other methods include establishing a Respiratory Disturbance Index (RDI) or an Oxygen Desaturation Index (ODI).

The sleep apnea to be treated can be any type of sleep apnea such as for example OSA, CSA or mixed apnea. However, it may be particularly suitable to treat a subgroup of sleep apnea patients.

The severity of sleep apnea may be quantified using the Apnea Hypopnea Index (AHI) in accordance with C. Iber *The AASM Manual for the Scoring of Sleep and Associated Events: Rules, Terminology, and Technical Specifications*. Ed.: American Academy of Sleep Medicine. AASM, Westchester, Ill. 2007. The last revision of the manual can be used.

The patient may preferably have sleep apnea with an AHI of at least 5 n/h, more preferably at least 15 n/h.

In one embodiment the patient has a mild sleep apnea with an AHI of from 5-14 n/h. In a preferred embodiment the patient has moderate sleep apnea (AHI=15-29n/h, in particular 15-20 n/h). In one embodiment the patient has severe sleep apnea (AHI=30 n/h or more).

In one embodiment the patient is preferably a male patient. The age of the patient may preferably be from 50 years and upwards, preferably from 50 to 65 years. The patient may be overweight, with a body mass index (BMI) of 25 or higher.

The drug sultiame, CAS 61-56-3, CID 5356 is known. The synthesis of sultiame is described in for example U.S. Pat. No. 2,916,489.

Sultiame may be administered by various routes. The most preferred route is by peroral administration. For this purpose a pharmacologically effective amount of sultiame is incorporated into a tablet, a lozenge, a capsule or similar dosage form comprising a pharmaceutically acceptable carrier. Peroral preparations designed for uptake through the oral mucosa, such as sublingual preparations, may be preferred.

Peroral preparations of sultiame, including preparations for sustained release, are known in the art. For preparing further preparations for per-oral administration reference is made to Pharmaceutical Dosage Forms: Tablets. Vol. 1-3, H A Lieberman et al., Eds. Marcel Dekker, New York and Basel, 1989-1990. In particular specific reference is made to chapter 7 (Special Tablets, by J W Conine and M J Pikal), chapter 8 (Chewable Tablets, by R W Mendes, OA Anaebonam and J B Daruwala), and chapter 9 (Medicated Lozenges; by D Peters).

A pharmacologically effective amount of sultiame may be administered to a patient in need thereof, in order to treat sleep apnea. A pharmacologically effective amount of sultiame is one that eliminates or substantially reduces apneic events over a period of sleep of from 1 hour to 10 hours.

The pharmacologically effective amount of sultiame in oral administration for treatment of sleep apnea will vary depending on factors such as the particular formulation of sultiame used, the route of administration, the release profile of the formulation into which it is incorporated, the severity of the disease, individual pharmacokinetic and -dynamic properties as well as the status of the patient. For instance, the dose range for peroral administration of sultiame to an adult, otherwise healthy person may be from 50 to 800 mg per 24 hours, or from 80 to 1000 mg/24 hours, more preferably 70 to 500 mg/24 hours, more preferably from 75 mg to 300 mg/24 hours, more preferably from 80 mg to 250 mg/24 hours and most preferably from 90 mg to 220 mg/24 hours.

In certain embodiments a high dose of sultiame may be preferred in order to treat sleep apnea. Thus in one embodiment the daily dose may be from 150 mg to 1000 mg, more preferably from 175 mg to 1000 mg, more preferably from 200 mg to 1000 mg, even more preferably from 250 mg to 1000 mg, even more preferably 300 mg to 1000 mg, and most preferably from 500 mg to 1000 mg.

Alternatively, in order to avoid side effects, the highest daily dose may be 800 mg, more preferably 600 mg, and most preferably 400 mg.

The appropriate dose range for the compound can be established in routine experiments.

The half-life of sultiame in plasma is about 24 hrs. The pharmacologically effective dose may preferably be taken once daily.

Also preferred is topical administration by, for example, transdermal administration. The transdermal formulation is specifically advantageous in regard of simplicity and from a patient comfort standpoint. It may, for instance, take the form of a transdermal patch.

In addition to the methods of administration of the compound of the invention mentioned above also parenteral, intranasal, and rectal administration can be useful, as well as administration by inhalation.

The timing of the administration of sultiame according to the invention will depend on the formulation and/or route of administration used. In the majority of cases sultiame will be administered as a long-term treatment regimen, whereby pharmacokinetic steady state conditions will be reached.

It is preferred that the therapeutically effective dose is effective during a substantial portion of a single sleep period, which may be from 1 hour to 10 hours. The substantial portion may be 50%, more preferably 80%, of said sleep period.

Moreover it is preferred that sultiame is used as a single agent, i.e. as the single active compound in a pharmaceutical composition. Excipients are not considered to be active compounds.

The administration of sultiame can be combined with an intraoral device or PAP treatment, in particular in patients with insufficient user time with the intraoral device or PAP treatment or with so called residual sleep apnea due to insufficient effectiveness on intraoral device or PAP treatment.

There is also provided a method for diagnosis of sleep apnea. Sultiame may be used for diagnosing sleep apnea and to distinguish sleep apnea from other types of sleep disorders. The diagnostic method comprises administrating a pharmacologically effective dose of sultiame to a person with manifest or suspected sleep apnea in increasing amounts prior to, or during, sleep. The observation of a reduction in the severity and/or number of sleep disordered breathing events or reduced sleepiness/increased alertness during daytime or altered activity of the carbonic anhydrase system or surrogate markers thereof (e.g. μl bicarbonate in the blood) following upon such administration is indicative of sleep apnea.

EXAMPLES

Example 1, Repeated Dosing of Sultiame in Obstructive Sleep Apnea

Male, 51 years, BMI 28.3 kg/m$^2$. The subject was a non-smoker and there was no history of cardiovascular or metabolic disease and no regular medication. This subject presented with a history of snoring, witnessed apneas, and increased daytime sleepiness. He had previously tested both CPAP and mandibular advancement therapy with moderate regression of symptoms. The subject had experienced intolerable side effects including dry airways and sneezing caused by CPAP therapy. He had experienced discomfort from the temporomandibular joints following use of an intraoral device for mandibular advancement.

A sleep study performed some three years previously provided a diagnosis of mild to moderate sleep apnea with an Apnea Hypopnea Index (AHI) of 17.4 n/h. There had been a weight gain corresponding to 2 kg during the last three years.

It was decided that sultiame should be tested. Repeated sleep studies were undertaken before and after therapy with sultiame. The repeated baseline assessment showed an AHI of 16.6 n/h (central AHI 3.2 n/h and obstructive AHI 12.4 n/h), mean oxygen saturation 95.3%, lowest saturation 87%, periodic breathing pattern during the complete recording night was 14.3 minutes.

Sultiame was started at a dose of 100 mg orally once daily and a new recording was undertaken after 5 days of treatment. This second assessment provided the following values: AHI 9.8 n/h (central AHI 2.2 n/h and obstructive AHI 7.6/h), mean oxygen saturation 95.8%, lowest saturation 89%, and periodic breathing pattern 10.1 minutes. There was no weight change recorded during these 5 days but there was a general resolution of daytime symptoms of sleepiness reported.

Following this assessment the daily dosage of sultiame was increased to 200 mg once daily for 14 days until the third assessment was performed. At this occasion the AHI was 4.2 n/h (central AHI 1.2 n/h, obstructive AHI 3.0 n/h), mean oxygen saturation 96.7%, lowest saturation 90% and the periodic breathing pattern had a duration of 2.8 minutes. There had been a weight reduction corresponding to 1.2 kg This example illustrated that sultiame reduced AHI in a dose-dependent manner as the effect of 200 mg once daily exceeded that seen after 100 mg once daily. Further, this effect comprised both obstructive and central breathing events during sleep as well as episodes of periodic breathing. Thus, both OSA and CSA were treated. These effects occurred without any concomitant change in body weight.

Example 2, Long Term Effect of Sultiame and Acetazolamide in Obstructive Sleep Apnea Two male subjects aged 51 and 61 years. BMI was 28.3 kg/m² and 26.1 kg/m², respectively. Both subjects were non-smokers and neither had any history of cardiovascular or metabolic disease. No regular medication was used. Obstructive sleep apnea had previously been diagnosed in these subjects on repeated recordings. The most recent recordings undertaken within 7 days prior to the experiment showed mild to moderate sleep apnea with an Apnea Hypopnea Index (AHI) of 17.4 n/h and 15.2 n/h, respectively. The oxygen desaturation index (ODI) recorded on the same study nights was 16.6 n/h and 12.6 n/h, respectively.

Treatment was initiated with acetazolamide 250 mg orally o.d. and the dose was rapidly increased to 500 mg o.d. On this dose both subjects developed peripheral paraesthesia with creeping sensory sensations bilaterally in hands and feet. These side effects were recognized as those typically reported by patients treated with acetazolamide. Repeated studies of respiration during sleep were prompted in both subjects and these took place 10 and 16 days, respectively, after the start of medication. At these occasions the recorded AHI was 13.4 n/h and 10.2 n/h, respectively. The oxygen desaturation index (ODI) recorded on the same study nights was 12.6 n/h and 9.2 n/h, respectively.

Medication with acetazolamide was interrupted and five days later therapy with sultiame 100 mg orally o.d. was initiated. Body weight was documented.

Sultiame was gradually titrated to a single daily dose of 200 mg, given for three months. The medication was well tolerated by both subjects and the paraesthesia reported during acetazolamide therapy were not reported after sultiame. A repeat sleep study was carried out at day 89 and 90 following onset of medication, respectively. At this occasion body weight had deceased with 3.2 and 2.8 kg, respectively, and both subjects reported a general reduction of hunger and craving. The AHI at follow-up was 7.6 n/h and 6.5 n/h. Both subjects reported reduced snoring and there was a reduction of daytime sleepiness in both cases. Reports from spouses suggested a reduction of snoring. Thus, sultiame was considerably more effective than acetazolamide in decreasing sleep apnea and had fewer side effects.

The results from Example 1 and 2 are summarized in table 1, below, where the results are further compared with data reflecting the effect of acetazolamide, topiramate and zonisamide in sleep apnea.

TABLE 1

|  | Sultiame | Acetazolamide | Acetazolamide | Topiramate | Zonisamide |
|---|---|---|---|---|---|
| Reference | Examples 1 and 2 above (n = 3) | Example 2 above | Meta data from 9 publications (n = 268) | Unpublished data (n = 4) | Eskandari et al. (n = 13) |
| Reduction in AHI | 62.7% | 28.0% | 37.3% | 28.0% | 20.7% |
| Reported adverse events. Frequency (n/patient) | 0% | 1.0/patient | 1.08/patient | 0.75/patient | 0.44/patient |
| Summary of efficacy/side effect ratio | | | | | |
| Efficacy AHI reduction (rating 0-3) # | 3 | 1 | 2 | 1 | 1 |
| Side effect paresthesia (P) (scale 0-3) ^ | 1 | 4 | 4 | 3 | 2 |
| Side effect cognitive dysfunction (C) (scale 0-3) ^ | 1 | 2 | 2 | 4 | 4 |
| Side effect total rating (T) (scale 0-3) * | 1 | 2.7 | 2.7 | 3.7 | 3.3 |
| Efficacy/side effect ratio | 3/1 = 3 | 1/2.7 = 0.38 | 2/2.7 = 0.74 | 1/3.7 = 0.27 | 1/3.3 = 0.30 |

\# = AHI reduction 0-5 < % = 0, 5-<30% = 1, 30-<50% = 2, ≥50% = 3
^ = side effect scale: 1 = none, 2 = low, 3 = medium, 4 = high
\* = ratio of severity rating paraesthesia plus 2 times severity cognitive rating dysfunction divided by three (T = (P + 2C)/3).

Table illustrates a higher reduction in AHI is a patients with obstructive sleep apnea after sultiame (62.7% reduction) compared with acetazolamide (37.3% reduction), topiramate (28.0% reduction) and zonisamide (20.7% reduction). In addition, and importantly, adverse effects were not observed after administration.

Example 3 Determination of Carbonic Anhydrase Activity in Venous Blood Obtained from a Patient with Obstructive Sleep Apnea. Effect of Sultiame and Acetazolamide Carbonic anhydrase (CA) activity was assessed in human plasma from an apnea patient using a method previously described in detail (Teng et al, Sleep 2016). This method was modified to permit addition of an aqueous solution of sultiame or acetazolamide in the reaction vessel to yield final concentrations of $5 \times 10^{-9}$, $1 \times 10^{-9}$, $5 \times 10^{-10}$, $1 \times 10^{-10}$, $5 \times 10^{-11}$ or $1 \times 10^{-11}$ M of the respective compound before addition of the diluted venous blood sample. In the current experiment the blood was collected from a single patient with obstructive sleep apnea and associated intermittent hypoxic episodes during sleep (age 50 yrs, AHI 35, ODI 31, lowest recorded oxygen level during sleep 79%, mean oxygen saturation during sleep 90.2%). The blood sample (antecubital vein) was collected in an EDTA-coated tube, stored within 30 min at −20° C. and subsequently transferred to −70° C. Prior to analysis, the sample was slowly thawed, refrozen and re-thawed on ice in order to obtain hemolysis. The assay was adapted from a method previously described by Everaert et al (ref in Teng et al, Sleep 2016). In detail, a buffer consisting of 0.02M HEPES, 0.02M MES, 0.035M KCl and 0.015M NaCl with a balanced capacity in the pH 6-8 range was prepared. The subsequent analysis was conducted on ice in order to maintain a temperature of around 0-1° C. A separate solution constituting of 200 ml of 0-1° C. distilled water was continuously flushed with 100% $CO_2$ and kept at 0-1° C. for at least 30 min. The blood sample was diluted (1:2000) in saline (0.9%) and 10 ml of the sample was applied into a separate reaction vessel containing 10 ml of the buffer solution. An aqueous solution (volume 1 ml) containing sultiame or acetazolamide was added to the reaction vessel. A calibrated pH meter (Docu-pH+, Sartorius, Sweden) was used to continuously monitor pH in the reaction vessel. A baseline pH of 8.00±0.03 was established during approximately 5 min at 0-1° C. 10 ml of the $CO_2$/distilled water solution was rapidly added into the reaction vessel to yield a final volume of 30 ml. The pH in the reaction vessel was continuously monitored at 1 Hz during 120 s. The analysis method had previously been calibrated by duplicate samples and repeated measurements. The intra- and inter assay variability was 5.0% and 7.6%, respectively. pH curves were plotted and analysed (FIG. 1). In order to reflect time of the catalysed reaction the area under the curve (AUC, range 802-837) was calculated as the sum of all pH assessments during 120 sec. Hence, a higher CA activity corresponds to a lower calculated value (shorter reaction time). For illustrative purposes CA activity was defined in arbitrary units as 850-AUC.

The experiment illustrates an approximately 36% more potent CA activity inhibition in blood obtained from a patient with obstructive sleep apnea after sultiame (reduction from 32 to 15, 53% reduction) compared with acetazolamide (reduction from 32 to 19.5, 39% reduction). In addition, the peak inhibition of activity was higher after sultiame compared with acetazolamide (15 units compared with to 19.5 units).

Example 4

A clinical trial was carried out to assess the potential side effects of a high dose of sultiame. Most earlier clinical trials have been carried out in patients diagnosed with epilepsy. The goal of this study was to investigate the tolerability of sultiame in non-epileptic patients.

The trial involved 16 healthy volunteers. 200 mg of sultiame was administered to each volunteer two times (once with and once without prior food intake). The administration was carried out without ramping up the dose. There were only two reports of adverse events in this group of 16 volunteers (32 dosing occasions, 12.5% of individuals or 6.25% of dosing occasions). These adverse events were limited to short periods of headache, which occurred when the drug was administered without food. The headache resolved within a short time frame. The trial demonstrated excellent tolerability of sultiame at high doses.

The invention claimed is:

1. A method for treatment of sleep apnea comprising administering, to a patient in need of treatment of sleep apnea, a therapeutically effective amount of sultiame.

2. The method for treatment of sleep apnea according to claim 1, where the sleep apnea is obstructive sleep apnea, central sleep apnea or mixed sleep apnea.

3. The method for treatment of sleep apnea according to claim 1, where the patient has an Apnea Hypopnea Index of 15 n/h or more.

4. The method for treatment of sleep apnea according to claim 1, where the patient has an Apnea Hypopnea Index of from 15 n/h to 29 n/h (moderate sleep apnea).

5. The method for treatment of sleep apnea according to claim 1, where the patient is a male patient.

6. The method for treatment of sleep apnea according to claim 1, where the patient has a body mass index of at least 25.

7. The method for treatment of sleep apnea according to claim 1, where the administering is peroral.

8. The method for treatment of sleep apnea according to claim 1, where a daily dose is from 80 mg to 250 mg.

9. The method for treatment of sleep apnea according to claim 1, where the sultiame is administered in a daily dose from 150 mg to 1000 mg.

10. The method for treatment of sleep apnea according to claim 1, where the sultiame is administered in a daily dose from 300 mg to 1000 mg.

11. The method for treatment of sleep apnea according to claim 1, where the sultiame is administered in a daily dose from 500 mg to 1000 mg.

* * * * *